United States Patent
Gochberg et al.

(10) Patent No.: US 12,320,767 B2
(45) Date of Patent: Jun. 3, 2025

(54) GAS VOLUME FRACTION MEASUREMENT AND CALIBRATION

(71) Applicant: Owens-Brockway Glass Container Inc., Perrysburg, OH (US)

(72) Inventors: Lawrence Gochberg, Sylvania, OH (US); Todd Coleman, Wayne, OH (US); Walter Anderson, Maumee, OH (US); Stephen Graff, Maumee, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 200 days.

(21) Appl. No.: 18/106,000

(22) Filed: Feb. 6, 2023

(65) Prior Publication Data

US 2024/0264105 A1  Aug. 8, 2024

(51) Int. Cl.
*G01N 27/07* (2006.01)
*G01N 27/04* (2006.01)
*G01N 33/38* (2006.01)

(52) U.S. Cl.
CPC .......... *G01N 27/07* (2013.01); *G01N 27/045* (2013.01); *G01N 33/386* (2013.01)

(58) Field of Classification Search
CPC  G01R 33/00; G01R 33/0035; G01R 33/0023; G01N 27/07; G01N 27/045; G01N 33/386
See application file for complete search history.

(56) References Cited

U.S. PATENT DOCUMENTS

| | | | |
|---|---|---|---|
| 3,339,138 A * | 8/1967 | Baker | G01N 27/07 324/717 |
| 4,282,481 A | 8/1981 | Dunn | |
| 5,289,716 A * | 3/1994 | Schumacher | G01N 11/12 73/54.15 |
| 6,577,112 B2 | 6/2003 | Lvovich et al. | |
| 2005/0138965 A1 | 6/2005 | Freeman | |
| 2009/0111117 A1 | 4/2009 | Chung et al. | |

(Continued)

FOREIGN PATENT DOCUMENTS

| | | |
|---|---|---|
| DE | 19806476 C1 | 10/1999 |
| WO | WO9002941 A1 | 3/1990 |

OTHER PUBLICATIONS

H.C. Yang, D.K. Kim, M.H. Kim "Void fraction measurement using impedance method" Department of Mechanical Engineering, Pohang University of Science and Technology, San 31, Hyoja Dong, Pohang, 790-784 (Year: 2003).*

(Continued)

*Primary Examiner* — Jermele M Hollington
*Assistant Examiner* — Taqi R Nasir

(57) ABSTRACT

A system and method of determining a gas volume fraction in a conductive liquid includes: immersing a first electrode in the conductive liquid, wherein the first electrode is electrically connected to a resistor and a voltage source; immersing a second electrode electrically connected to the voltage source in the conductive liquid; determining resistance information indicative of an electrical resistance of the conductive liquid between the first electrode and the second electrode; and determining a gas volume fraction in the conductive liquid based on the measurement.

28 Claims, 9 Drawing Sheets

(56) References Cited

U.S. PATENT DOCUMENTS

2014/0123751 A1    5/2014  Lu
2017/0103821 A1*   4/2017  Maldonado Saavedra ..................
                                                        G01F 1/74

OTHER PUBLICATIONS

PCT Search Report and Written Opinion, Int. Application No. PCT/US2024/013787, Int. Filing Date: Jan. 31, 2024, Applicant: Owens-Brockway Glass Container Inc., Mailed: May 23, 2024.
H. C. Yang, "Void Fraction Measurement Using Impedance Method", vol. 14, No. 4-5, Jul. 3, 2003, pp. 151-160, XP093161017.
M. Fossa, "Design and Performance of a Conductance Probe for Measuring the Liquid Fraction in Two-Phase Gas-Liquid Flows", Flow Measurement and Instrumentation, vol. 9, No. 2, Nov. 24, 1998, pp. 103-109, XP093160719.

* cited by examiner

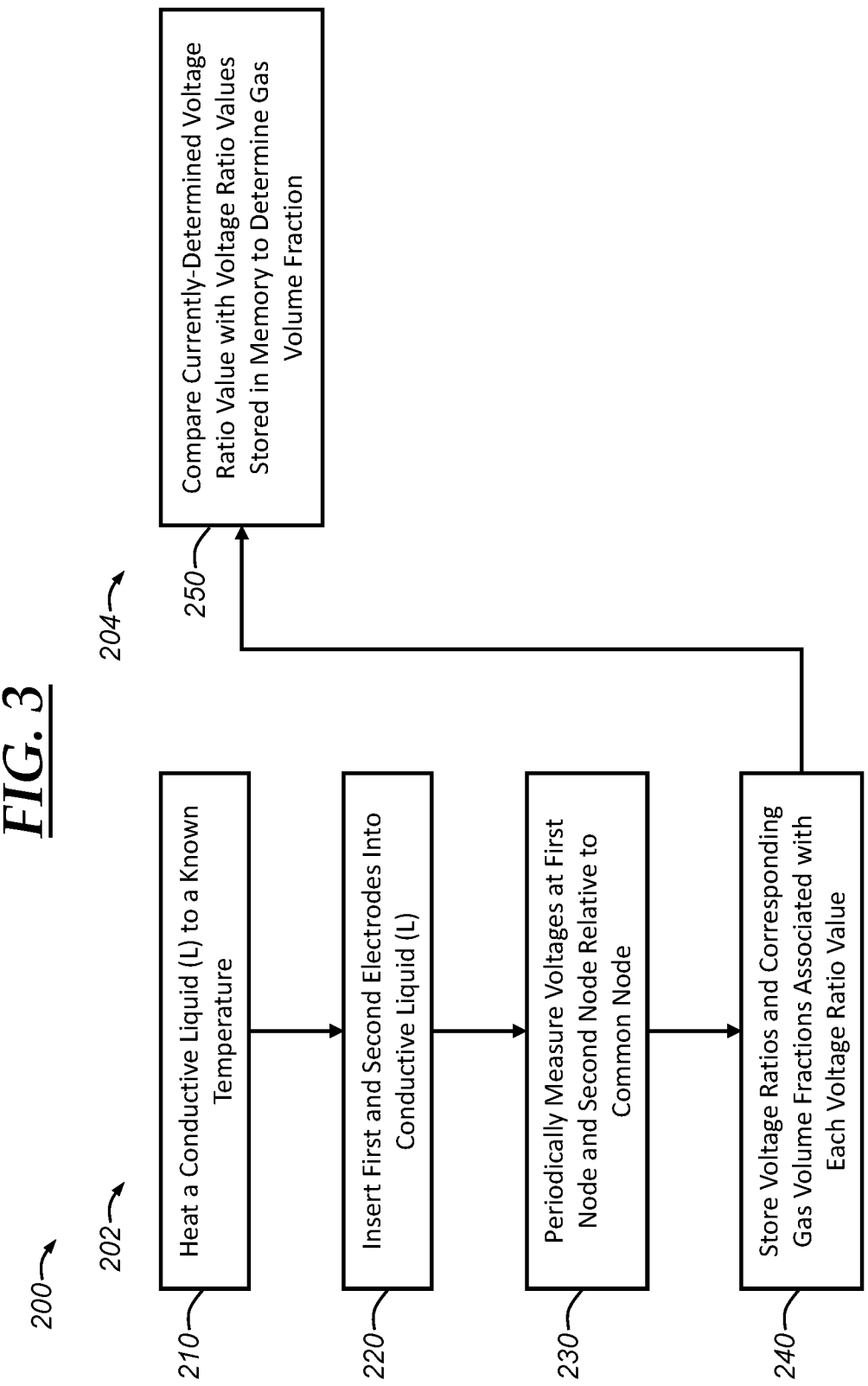

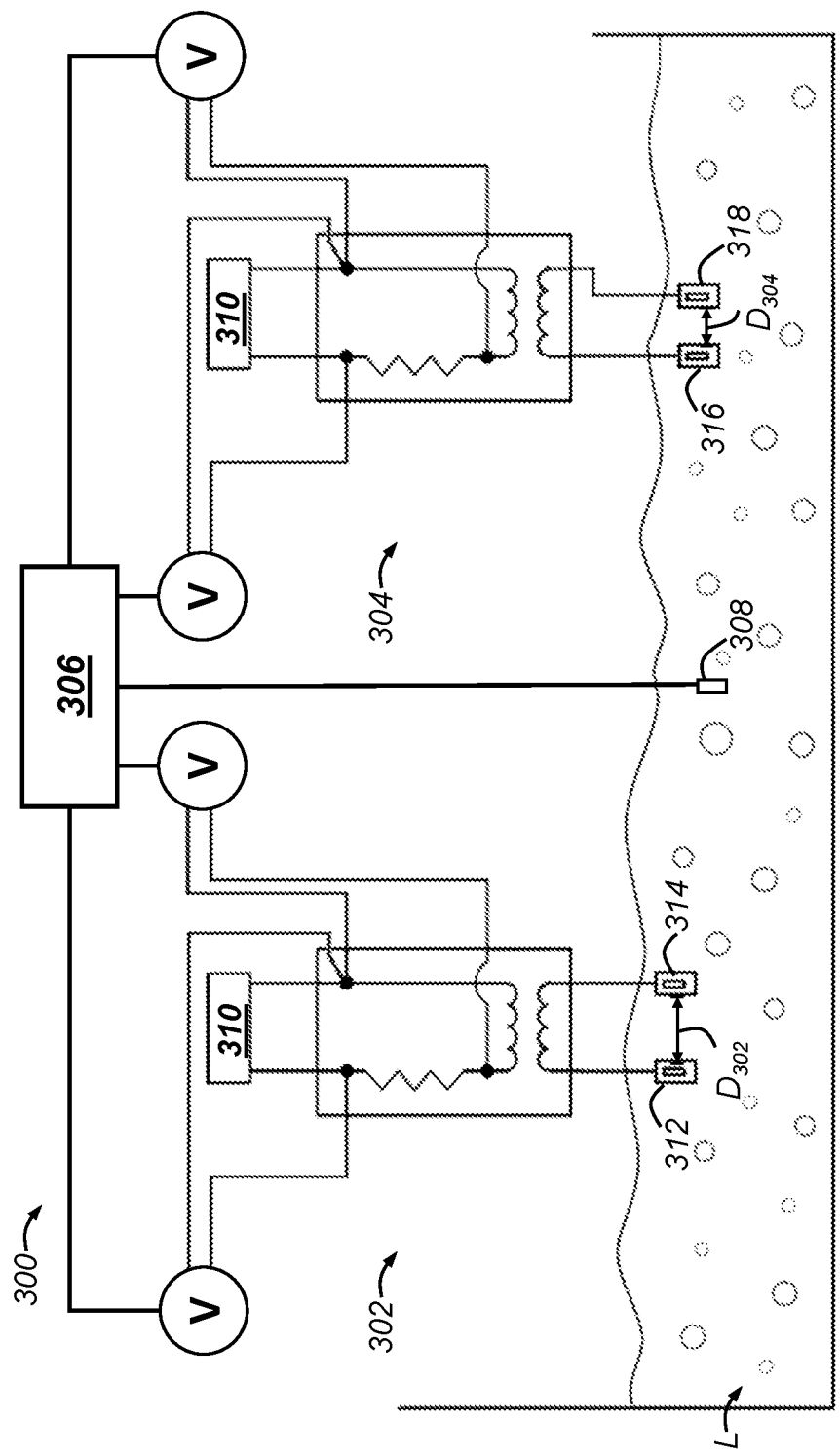

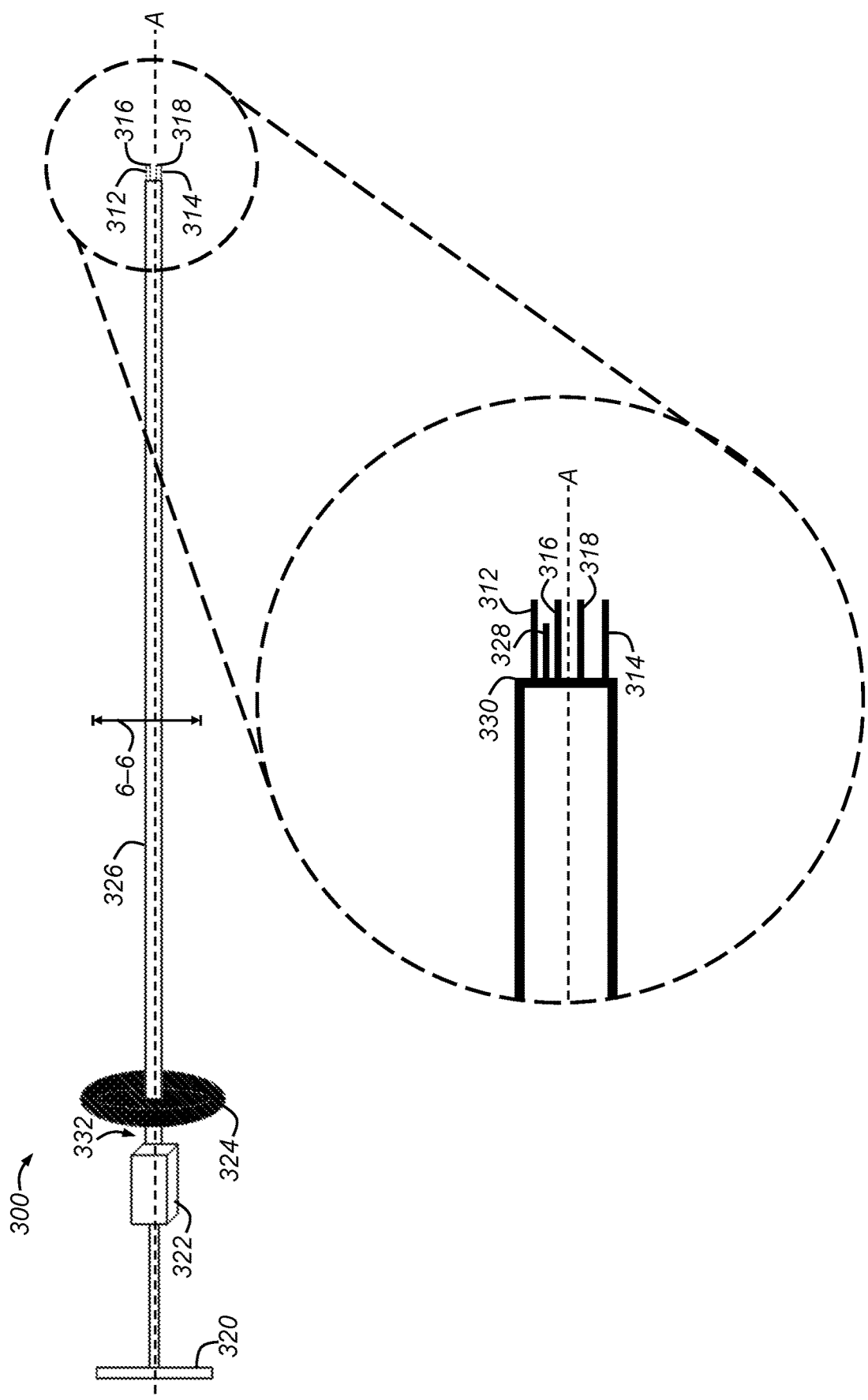

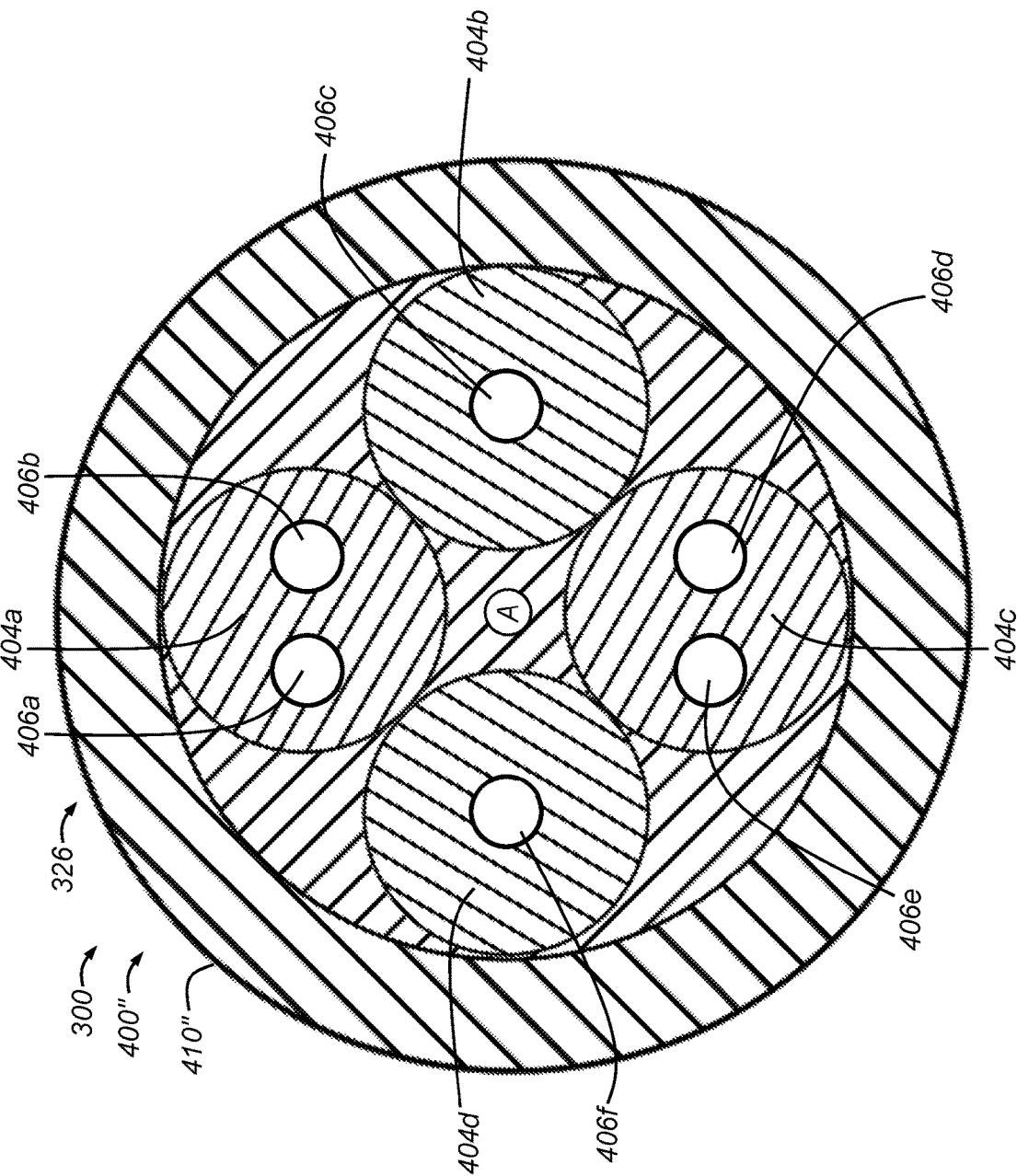

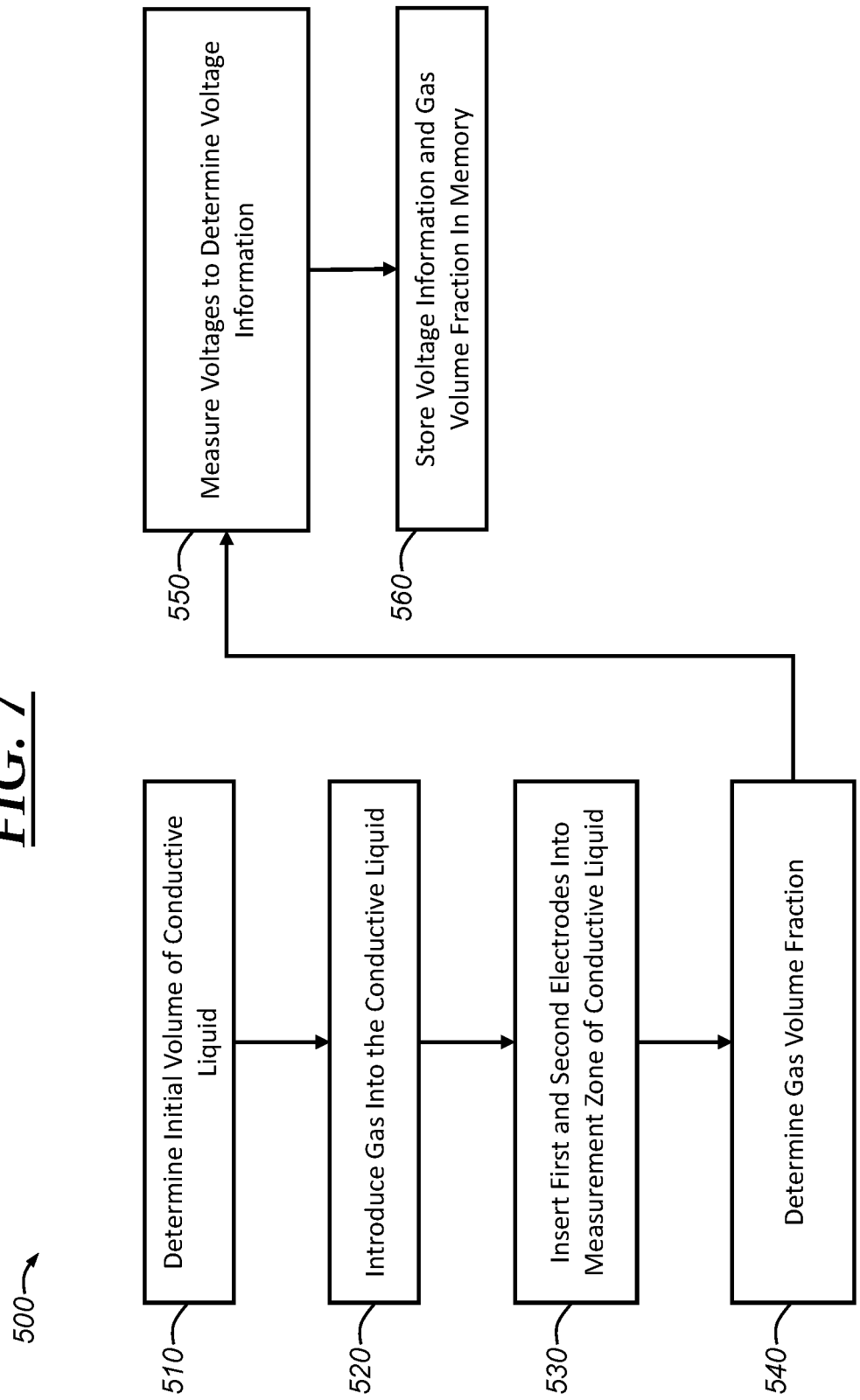

GAS VOLUME FRACTION MEASUREMENT AND CALIBRATION

TECHNICAL FIELD

The present application relates to systems, equipment, and methods for determining characteristics of a multiphase mixture and, more particularly, to systems, equipment, and methods for measuring a gas volume fraction in conductive liquid and related calibration systems, equipment, and methods.

BACKGROUND

Manufacturing glass involves melting sand and optionally other elements into a molten state in response to the application of heat. This yields a molten glass that is monitored to determine its composition during the manufacturing process allowing the manufacturer to modify the temperature and/or the composition of the glass. In addition to the elements that make up the molten glass, it also includes a gas component in the form of bubbles dispersed into the molten glass and this multiphase liquid having gas bubbles is a type of conductive liquid. As the molten glass is heated, the bubbles are slowly removed to create a glass product without blisters. Typically, two vertically-oriented probes having a fixed distance between them are immersed into the molten glass and output a binary signal indicating whether or not the sensors are in contact with molten glass or a gas. This binary signal indicating the absence/presence of gas is further analyzed to determine how much gas the molten glass includes.

For example, as a gas bubble passes by and contacts each of the probes, an amount of time can be measured from the point at which the bubble passes from the first probe to the point at which the bubble contacts the second probe. Given a known distance between these probes, it is possible to determine the velocity of the gas bubble. And an estimate of the chord length of the gas bubble is generated using a measured amount of time the gas bubble remains on a probe. A probability density function is determined based on the velocity and chord length of the gas bubbles. However, some imprecision exists using these techniques. The gas bubbles may be diminutively sized such that they are not pierced by a probe but instead pass by the probe without contact making it difficult or even sometimes impossible to determine accurate velocity or chord length. So, according to such conventional methodologies employing a binary signal, unless the gas bubble size is greater than a particular value and uniformly distributed, the accuracy of gas measurement of the liquid may not be particularly accurate. It would be helpful to measure the gaseous properties of molten glass with greater accuracy regardless of the heterogeneity of gas bubble size and/or distribution.

SUMMARY OF THE DISCLOSURE

In one embodiment, a method of determining a gas volume fraction in a conductive liquid is provided, and the method includes immersing a first electrode in the conductive liquid, wherein the first electrode is electrically connected to a resistor and a voltage source; immersing a second electrode electrically connected to the voltage source in the conductive liquid; determining resistance information indicative of an electrical resistance of the conductive liquid between the first electrode and the second electrode; and determining a gas volume fraction in the conductive liquid based on the measurement.

In another embodiment, a method of determining a gas volume fraction in a conductive liquid is provided, and the method includes immersing a first electrode in the conductive liquid, wherein the first electrode is electrically connected to a resistor and a voltage source; immersing a second electrode electrically connected to the voltage source in the conductive liquid; periodically measuring a first voltage at the first node relative to a common node and a second voltage at a second node relative to the common node; determining a plurality of resistances using the periodically measured first voltages and the periodically measured second voltages; associating a gas volume fraction with each resistance; storing the resistances and the associated gas volume fractions in a memory device; immersing the first electrode and the second electrode in a different conductive liquid; measuring a first voltage at the first node relative to a common node and a second voltage at a second node relative to the common node while the first electrode and the second electrode are immersed in the different conductive liquid; determining a resistance based on the first voltage and second voltage measured while the first electrode and second electrode are immersed in the different conductive liquid; comparing the resistance determined while the first electrode and second electrode are immersed in the different conductive liquid with the stored resistances and associated gas volume fractions; identifying a stored resistance that matches the resistance determined while the first electrode and second electrode are immersed in the different conductive liquid; and determining a gas volume fraction associated with the identified stored resistance.

In yet another embodiment, an electrical conductivity probe is provided for measuring a gas volume fraction in a conductive liquid includes a first electrode that is electrically connected to a resistor and a voltage source; a second electrode electrically connected to the voltage source; and a processor configured to obtain a first voltage measurement across a first node on the first electrode and a common node on the first electrode and a second voltage measurement across a second node on the second electrode and the common node, wherein the processor: determines an electrical resistance of the conductive liquid based on the first voltage measurement and the second voltage measurement when the first electrode and the second electrode are immersed in the conductive liquid; and determines a gas volume fraction in the conductive liquid based on the measurement.

BRIEF DESCRIPTION OF THE DRAWINGS

FIG. 3 is a flowchart depicting an embodiment of a method of determining a gas volume fraction in a conductive liquid;

FIG. 4 is diagram depicting an implementation of an electrical conductivity multiprobe device for measuring a gas volume fraction in a conductive liquid, according to one embodiment;

FIG. 5 is a diagrammatic view of the electrical conductivity multiprobe device of FIG. 3, according to one embodiment;

FIG. 6C is a second alternative sectional view taken along 6-6 of FIG. 5 showing portions of electrical conductivity probes included in the electrical conductivity multiprobe device of FIG. 4, according to one embodiment employing a third electrical conductivity multiprobe device configuration and a first tube in a tube construction;

FIG. 7 is a flowchart depicting an embodiment of a method of operating an electrical conductivity probe in calibration mode to obtain resistance information for an associated gas volume fraction of a liquid.

DETAILED DESCRIPTION

Figure 1:
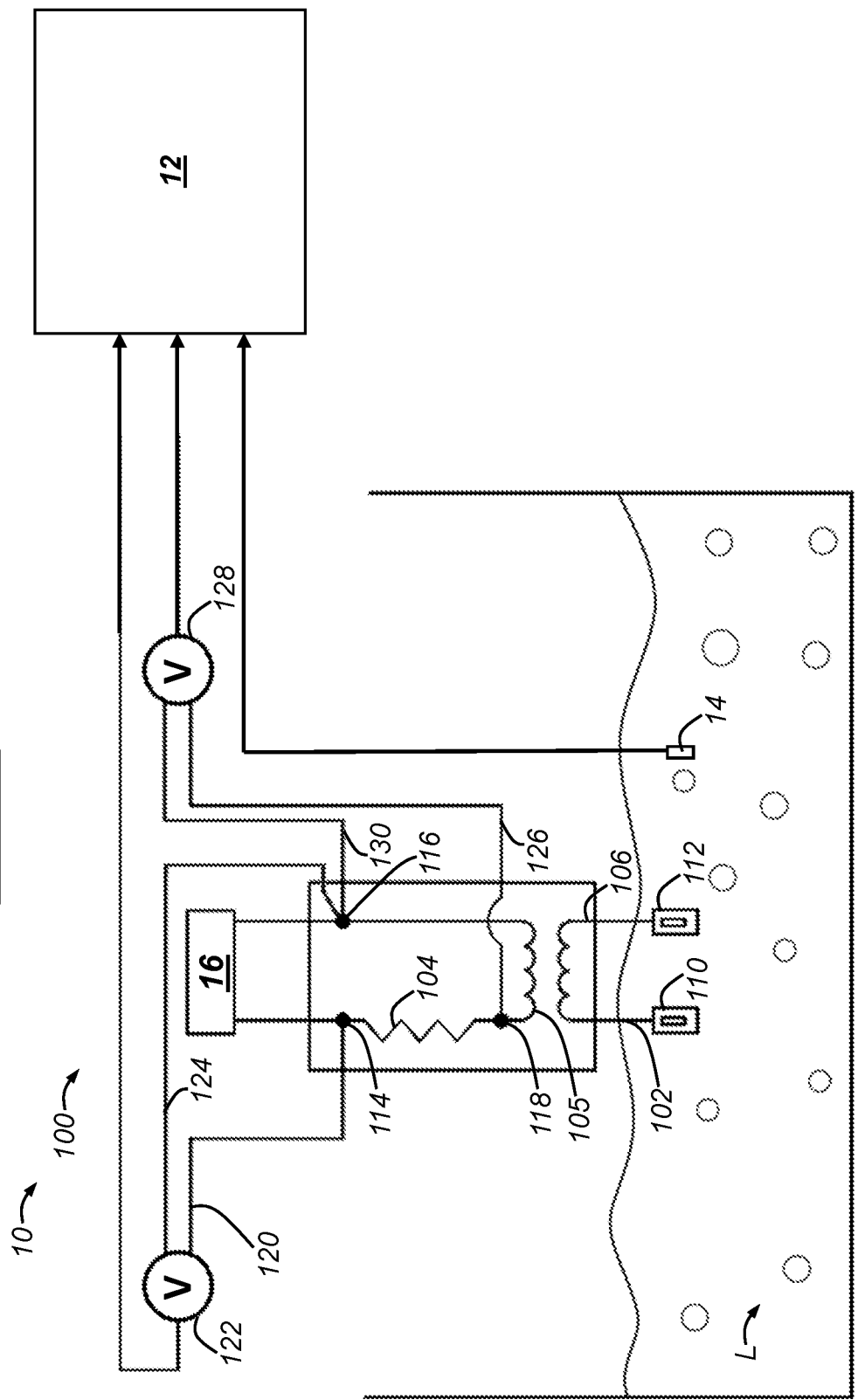
FIG. 1 is a diagram depicting an implementation of an electrical conductivity probe for measuring a gas volume fraction in a conductive liquid, according to one embodiment.

An electrical conductivity probe, and method for calibrating an electrical conductivity probe, is provided, where the electrical conductivity probe is used for measuring a bulk property of a multiphase or bubbly conductive liquid, in the form of a local gas volume or void fraction in the bubbly conductive liquid. As stated herein, the term "liquid" includes molten glass, a flowable glassy melt, and/or glass in a molten state. The electrical conductivity probe includes a first electrode and a second electrode, and is configured so to apply alternating current (AC) voltage across the first electrode and the second electrode and to measure a first voltage at the first electrode and a second voltage at the second electrode. The voltage across a resistor of a known value gives the current (measured in Ohms) in the system. The voltage across the probes then allows the conductivity of the glass to be determined. The level of conductivity, which may be represented by a resistance between the first voltage and the second voltage, then may be used to determine the gas volume fraction in the conductive liquid. The electrical resistance and the temperature of the glass may indicate the average gas volume fraction (i.e., amount of bubbles) in the liquid. According to embodiments, prior to measuring the gas volume fraction of a conductive liquid, the first electrode and the second electrode may be immersed in a calibrating liquid having a known temperature and a known composition. The resistance as indicated by (or other resistance information derived from) the voltages measured at the first and second electrodes may then be associated with the known gas volume fraction of the calibrating liquid. Different conductive liquids may be more or less conductive from compositional and temperature differences and amount of current drawn through the resistor can vary depending on the conductivity of the liquid and/or the amount of gas bubbles in the liquid.

A calibrated resistance is determined by measuring the current supplied, voltage across the resistor, and the voltage across the two electrodes while the electrodes are immersed in a calibrating liquid; this calibrated resistance, or other resistance information, may be recorded for later reference, such as for reference when using the probe in operation. This technique for obtaining calibrated resistance information may be repeated using different calibrating liquids, which could include liquids having the same or similar compositions but with different amounts of gasses. Later, when the first electrode and the second electrode are immersed in an unknown conductive liquid, the first voltage and the second voltage may be measured, the resistance between the first and second voltage may be determined and compared with one or more previously-determined calibrated resistances; based on this comparison, a gas volume fraction of the unknown conductive liquid may be determined. In embodiments, the electrical conductivity probe is used to effectively determine the gas volume fraction for conductive liquids in which the gas bubble size is small, such as when bubble size is less than 1 millimeter (mm) in chord length, and when the bubbles are heterogeneously dispersed within the conductive liquid. And the probes of the electrical conductivity probe can be oriented in various positions within a crucible holding the liquid without impeding performance.

According to some embodiments, an electrical conductivity multiprobe device incorporating multiple electrical conductivity probes, each of which operates as a separate probe having a pair of electrodes, may be used. In embodiments, the electrical conductivity multiprobe device includes a first electrical conductivity probe defined by two electrodes spaced apart at a first electrode distance and a second electrical conductivity probe defined by two electrodes spaced apart at a second electrode distance, where the second electrode distance is different than the first electrode distance. In one particular embodiment, for example, the first electrode distance is 7-9 millimeters (mm) and the second electrode distance is 14-20 mm, which may facilitate accurate and precise detection of relatively small bubbles and relatively large bubbles, respectively. As discussed more below, use of multiple probes and, in particular, use of multiple probes in a single conductivity multiprobe device, enables gas volume fractions to be more precisely and accurately obtained for a larger variety of gas bubble sizes and may be used to indicate the presence of a larger size distribution.

Turning to FIG. 1, an implementation of an electrical conductivity probe device 10 having an electrical conductivity probe 100 is shown for measuring a gas volume fraction of a conductive liquid (L). The gas volume may be in the form of gas bubbles in molten glass. The bubbles are generally spherical and rise vertically within the molten glass. The electrical conductivity probe device 10 also includes a processor 12, one or more thermocouples 14, and a power supply 16. The probe 100 includes a first electrode 102, a resistor 104, and a second electrode 106. In the illustrated embodiment, the first electrode 102 and the second electrode 106 are each electrically connected to a transformer 105 that provides physical isolation from the first electrode 102 and the second electrode 106.

The first electrode 102 and the second electrode 106 each terminate with a first immersion paddle 110 and a second immersion paddle 112, respectively, that are immersed in the conductive liquid (L). A voltage source, described in the present embodiment as the power supply 16, applies an alternating current (AC) voltage across the first electrode 102 and the second electrode 106 by applying the AC voltage to the transformer 105. The processor 12 obtains voltages between a first node 114 and a common node 116 on the second electrode 106 (a first voltage measurement) as well as a second node 118 on the first electrode 102 and the common node 116 (a second voltage measurement). The measured voltages can then be used by the processor 12 to generate a resistance and the resistance may be compared with reference resistance values stored in a memory device to determine a gas volume fraction of the conductive liquid (L). The electrical conductivity probe 100 will be discussed with reference to the immersion of a portion of the first electrode 102 and a portion of the second electrode 106, such as the first immersion paddle 110 and second immersion paddle 112, respectively, into a conductive liquid (L) comprising molten glass. However, it should be understood that the probe 100 could be used to determine the gas volume fraction of other conductive liquids. Those of ordinary skill in the art will recognize that the device 10 also may include suitable digital to analog converters, signal processing devices, etc.

Figure 2:
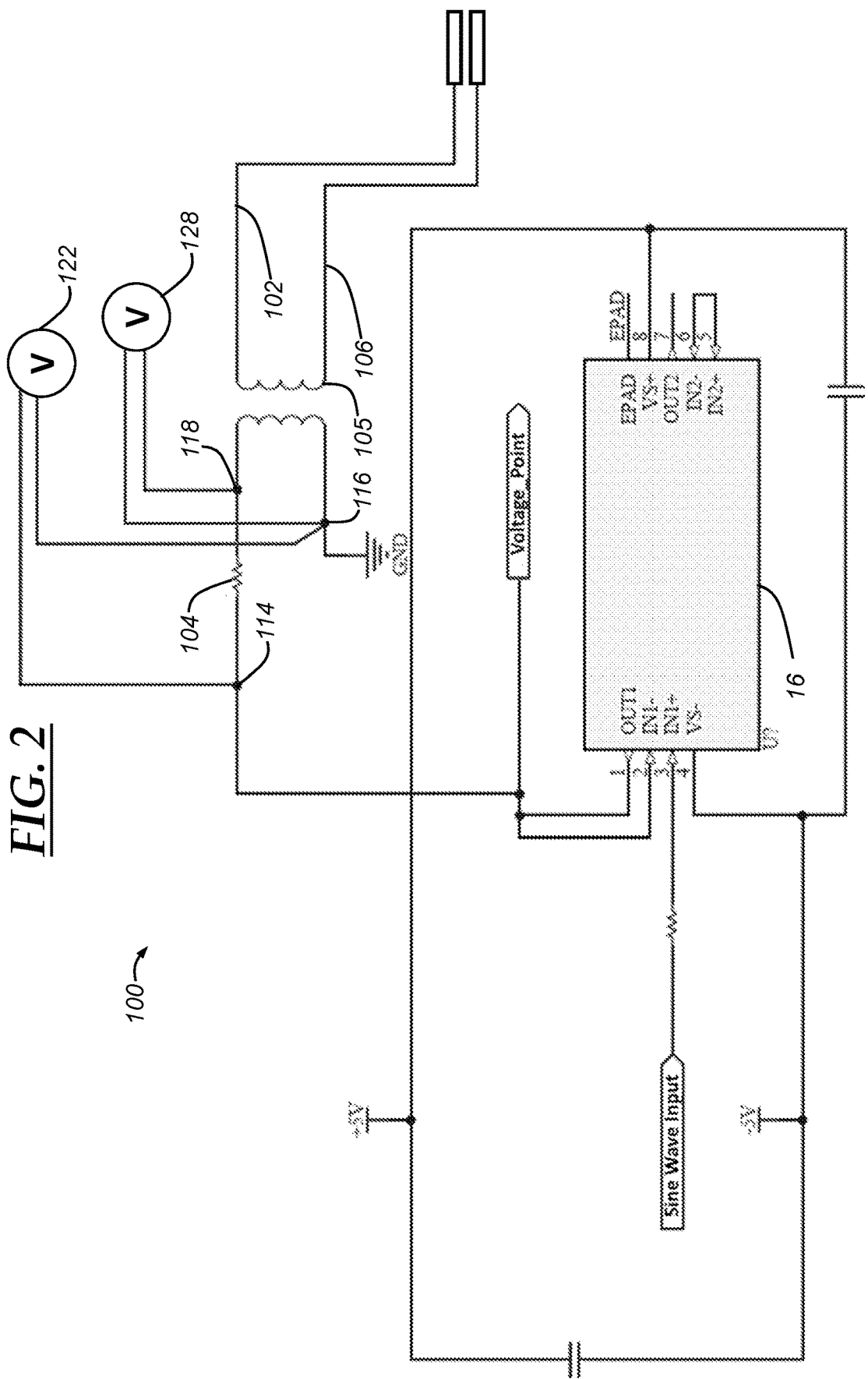
FIG. 2 is a schematic circuit diagram that may be used for the electrical conductivity probe of FIG. 1.

With reference to FIG. 2, and with continued reference to FIG. 1, there is shown a circuit schematic of the exemplary electrical conductivity probe 100 of FIG. 1, including the first electrode 102, the resistor 104, the transformer 105, the second electrode 106, the first node 114, the common node 116, and the second node 118. The electrical conductivity probe 100 is shown in FIG. 2 as including an Analog Devices™ AD8397 Rail-to-Rail, High Output Current Amplifier as the power source 16; of course, other power sources, including various AC power sources, may be used, according to embodiments. In one exemplary embodiment, the resistor 104 may be a 3 Ohm resistor having a fixed amount of resistance; in other embodiments, a 2-15 Ohm resistor may be used. In one exemplary embodiment, the power source may be used to provide AC power at between 1000-50,000 Hz. And, in an exemplary embodiment, an excitation voltage of one volt is provided through the transformer; however the excitation voltage may be any suitable value, such as those based on conductivity of the conductive liquid yielding currents and voltages with low enough noise levels to be readable. From the applied current and voltage, the observed resistance of the molten glass is typically between 5 and 15 Ohms, at least according to certain embodiments.

According to at least some embodiments, including the illustrated embodiment of FIG. 1, the electrical conductivity probe device 10 includes the thermocouple(s) 14, which are used for measuring temperature of the conductive liquid and, in at least some embodiments, a local temperature of the conductive liquid that is adjacent or near an electrode end of the probe device 10. In one embodiment, the electrical conductivity probe device 10 includes a single thermocouple 14. The thermocouple(s) 14 may be used to measure a temperature at a tip of the probe, such as at a location proximate to the tip or electrode end of the first electrode 102 and/or the tip or electrode end of the second electrode 106. According to some embodiments, an R type thermocouple may be used and, in other embodiments, an S type thermocouple may be used. In embodiments employing multiple thermocouples, different thermocouples, such as those of different types (e.g., R type, S type), may be employed. The thermocouple(s) 14 are connected to the processor 12 so that a measured temperature may be determined by the processor 12 and used as a part of determining a gas volume fraction and, in particular, may be used to correct inherent measured conductivities at a reference temperature to actual conductive liquid temperature. In embodiments, the thermocouple junction (measuring point) of the thermocouple is immersed in the conductive liquid at the same height as the electrode ends.

The first electrode 102 and second electrode 106 are made from an electrically-conductive material that is also resistant to high temperatures. The probe 100 is designed to operate in a kiln or furnace that heats the molten glass to temperatures above 1000° C. so the first electrode 102 and second electrode 106 can withstand these temperatures and still conduct electricity from the molten glass to the processor 12. The electrodes may be composed of platinum, alloys of platinum with rhodium, or the like. The first electrode 102 and the second electrode 106 may be immersed in the molten glass at a non-vertical orientation. According to conventional systems and methods, probes have relied on electrodes that are vertically aligned such that a gas bubble touching one electrode is later captured by another electrode. However, according to at least some embodiments of the present disclosure, the electric conductivity probe 100 may be oriented and/or positioned so that the first electrode 102 and the second electrode 106 may be oriented in any position without impeding performance. For example, the electrical conductivity probe device 10 may be tilted so that a central or longitudinal axis of the probe device 10 is obliquely angled relative to a vertical direction, which may be defined with respect to gravity.

According to embodiments, one end of the first electrode 102 and the second electrode 106 may be a point or, alternatively, a paddle-shaped terminal. The paddle shaped terminals, shown by the first immersion paddle 110 and the second immersion paddle 112, may have a length and width dimension such that they can be circular, square, or rectangular in profile. The first electrode 102 includes the resistor 104 electrically connected between the first node 114 and the second node 118. The resistor 104 can be implemented resistors of different resistance values. The transformer 105 is used to physically isolate portions of the device from the first electrode 102 and the second electrode 106 so that fluctuations in voltage or current do not cause harm to the electronics and circuitry. For example, the transformer 105 effectively blocks unwanted voltages present in the molten glass, for instance, voltages caused by boost electrode heaters, or galvanic potentials inherent in the glass melting process, or the like. The transformer 105 may block all DC voltages and low frequency AC voltages. The voltage source or power supply 16 electrically connects to the first electrode 102 and the second electrode 106 and applies a voltage across the first electrode 102 and the second electrode 106. The applied voltage can be an alternating current (AC) voltage, and not a direct current (DC) voltage. The amount of voltage applied to the first electrode 102 and the second electrode 106 by the voltage source can vary, but in this implementation the amount of voltage is 1-2 volts (V).

The processor 12 can be any type of device capable of processing electronic instructions including microprocessors, microcontrollers, host processors, controllers, vehicle communication processors, and application specific integrated circuits (ASICs). These devices typically include at least one input, at least one output, a memory device, and a bus that communicates between these elements. The processor 12 can also communicate with an external memory device that is capable of storing data and computer-readable instructions. The processor 12 executes various types of digitally-stored instructions, such as software or firmware programs stored in memory. For instance, processor 12 can execute programs or process data to carry out at least a part of the method discussed herein. The software or firmware can be implemented in a computer program product embodied in a computer readable medium and including instructions usable by the processor 12. The computer program product may include one or more software programs comprised of program instructions in source code, object code, executable code or other formats; one or more firmware programs; or hardware description language (HDL) files; and any program related data. The data may include data structures, look-up tables, or data in any other suitable format. The data can be stored internally at the processor 12 or in the external memory. The program instructions may include program modules, routines, programs, objects, components, and/or the like. The computer program can be executed on one computer or on multiple computers in communication with one another.

The program(s) can be embodied on computer readable media, which can be non-transitory and can include one or more storage devices, articles of manufacture, or the like. Exemplary computer readable media, also referred to simply as memory, include computer system memory, e.g. RAM (random access memory), ROM (read only memory); semiconductor memory, e.g. EPROM (erasable, programmable ROM), EEPROM (electrically erasable, programmable ROM), flash memory; magnetic or optical disks or tapes; and/or the like. The computer readable medium may also include computer to computer connections, for example, when data is transferred or provided over a network or another communications connection (either wired, wireless, or a combination thereof). Any combination(s) of the above examples is also included within the scope of the computer-readable media. It is therefore to be understood that the method can be at least partially performed by any electrical articles and/or devices capable of carrying out instructions corresponding to one or more steps of the disclosed method.

Electrical leads connect each of the first electrode 102 and the second electrode 106 to the processor 12 via attachments to the first node 114, the second node 118, and the common node 116. A first electrode lead 120 electrically links the processor 12 to the first node 114 by way of a voltmeter 122 and a first common electrode lead 124 electrically links the processor 12 to the common node 116 by way of the voltmeter 122. A second electrode lead 126 electrically links the processor 12 to the second node 118 by way of a voltmeter 128 and a second common electrode lead 130 electrically links the processor 12 to the common node 116 by way of the voltmeter 128. In the illustrated embodiment, the voltmeter 122 obtains a first voltage measurement that is taken across the resistor 104 and the voltmeter 124 obtains a second voltage measurement that is taken across the first electrode 102 and the second electrode 106. The first voltage measurement may be across the first node 114 on the first electrode 102 and a common node 116 on the first electrode 102 and the second voltage measurement may be across the second node 118 on the second electrode 106 and the common node 116. It should be appreciated that various types of voltmeters or mechanisms for measuring a voltage may be employed as the voltmeters 122, 128 and that, in some embodiments, the voltmeter 122 is separate and distinct from the voltmeter 128, but in other embodiments, the voltmeter 122 and voltmeter 128 are one and the same. In embodiments, there is only a single common electrode lead 124 that is used as the first common electrode lead 124 and the second common electrode lead 130, such as in embodiments where the voltmeter 122 and voltmeter 128 are one and the same. The processor 12 may determine the voltage across the resistor 104 by measuring the voltage at the first node 114 via the first electrode lead 120 relative to the voltage measured at the common node 116 via the first common electrode lead 124. And the processor 12 may also determine a voltage measured between the second node 118 and the common node 116 through use of the second electrode lead 126 and the second common electrode lead 130. The processor 12 may calculate a resistance using the reference voltage and the voltage across the resistor 104.

The resistance calculated by the processor 12 or current (derived from the calculated resistance) may be used in a variety of ways depending on whether the probe 100 is in a calibration mode or an operation mode. For example, the processor 12 may store the currently-measured resistance along with a known gas volume fraction value associated with that ratio in memory as part of a calibration mode. Or, as part of an operation mode, the processor may access a lookup table in memory containing a plurality of resistance values corresponding to gas volume fraction values for molten glass. The processor 12 may then compare the currently measured/calculated resistance with the resistance values in the lookup table to identify a match and then output the gas volume fraction corresponding to the matching resistance stored in memory.

It should be appreciated that the arrangement, number, and even configuration of components or elements, such as the processor 12, the thermocouple(s) 14, the power supply 16, and the voltmeters 122, 128 may vary according to different embodiments.

Turning to FIG. 3, an embodiment of a method 200 of determining a gas volume fraction in a conductive liquid is shown, which includes a calibration process 202 and an operation process 204. In the calibration process 202, which includes steps 210-240, resistance value(s) are determined and are each stored in memory along with an associated gas volume fraction. In the operation process 204, which includes step 250, a resistance is determined based on measuring voltages across the first node and common node and across the second node and common node. After the calibration process 202 and prior to the operation mode 204 and/or as a part of the operation mode 204, an operating conductive liquid may be initially heated and the electrical conductivity probe may be inserted into the heated operating conductive liquid. Then, the voltages may be measured and the gas volume fraction determined in step 250.

The method 200 begins at step 210 by heating a conductive liquid (L) at a known temperature. In this implementation, a ceramic crucible containing molten glass may be heated inside of a constant temperature furnace operating at a temperature of 1350° C. Proceeding to step 220, the first electrode 102 and the second electrode 106 of the probe 100 are inserted into the conductive liquid (L) after the molten glass has been heated for a period of time and is beginning to fine the gas bubbles. The temperature of the glass may be monitored using the probe 14. The method 200 then proceeds to step 230.

At step 230, the probe 100 periodically measures voltages at the first node 114 and the second node 118 relative to the common node 116. A resistance derived from the voltage measured across the resistor 104 at the first node 114 and the common node 116 and the voltage measured between the second node 118 and the common node 116 may periodically be determined and stored in memory. As the furnace continues to heat the molten glass, the gas volume fraction of the molten glass changes. Each time the probe 100 determines a resistance, the molten glass comprises a different gas volume fraction. Thus, each time the resistance is calculated the value can correspond to a particular gas volume value for that particular conductive liquid. If the gas volume fraction of the molten glass is known, it is stored in memory with the resistance. The periodic calculation of resistances as time passes and the change in gas volume fraction of the molten glass each time the resistances are calculated may be created as a reference to be used later for determining a gas volume fraction that corresponds to a particular resistance determined by the probe. The resistances and the corresponding gas volume fractions associated with each resistance value (and fluid temperature value) may be stored in memory accessible by the probe 100 at step 240. The method 200 proceeds to step 250.

At step 250, the probe 100, used later in an operation mode, compares a currently determined resistance measured from a conductive liquid to resistances stored in memory to determine the gas volume fraction of the conductive liquid. By comparing currently-gathered resistances with previously-stored resistances gathered during a calibration mode, the probe may determine an existing gas volume fraction of the conductive liquid. When the processor 12 finds a match between the currently-gathered resistance and one of the resistances stored in memory (and which may take into consideration corrections for temperature based on readings from the thermocouple), the processor 12 may access a gas volume fraction associated with the matching resistance and output that value as the current gas volume fraction of the conductive liquid. The method 200 then may end.

Turning to FIG. 4, there is shown an electrical conductivity multiprobe device 300 having multiple electrical conductivity probes, either or both of which may be the electrical conductivity probe 100 discussed above. The electrical conductivity multiprobe device 300 includes two electrical conductivity probes 302, 304, as depicted in the illustrated embodiment. The electrical conductivity multiprobe device 300 further includes a processor 306, one or more thermocouples 308, and power supplies 310, each of which are analogous to the processor 12, thermocouple(s) 14, and power supply 16 of the electrical conductivity probe device 10 discussed above, respectively; that relevant discussion of the electrical conductivity probe device 10 is hereby additionally attributed to the electrical conductivity multiprobe device 300 to the extent such discussion is not inconsistent with the discussion below. Although there are four voltmeters shown, each of which are used to calculate a voltage over a different path of a respective one of the probes 302, 304, it should be appreciated that any suitable number of such devices and/or other circuitry or components may be used according to various embodiments. It should be appreciated that FIG. 4 is presented primarily for purposes of demonstrating certain features and technical aspects of this disclosure, and that the arrangement, number, and even configuration of components or elements, such as the probes 302, 304, the processor 306, the thermocouple(s) 308, the power supply 310, and the voltmeters may vary according to different embodiments.

Each of the two electrical conductivity probes 302, 304 is an electrical conductivity probe and may be configured according the electrical conductivity probe 100, at least according to some embodiments. The first electrical conductivity probe 302 includes a first electrode 312 and a second electrode 314, and the second electrical conductivity probe 304 includes a first electrode 316 and a second electrode 318. The electrodes 312-318 of the first and second electrical conductivity probes 302, 304 may be housed in a common housing, which is discussed in more detail below. According to one embodiment, the electrodes 312, 314 of the first electrical conductivity probe 302 are spaced apart at a first distance $D_{302}$ and the electrodes 316, 318 of the second electrical conductivity probe 304 are spaced apart at a second distance $D_{304}$, where the second distance is different than the first distance. However, in embodiments, the first distance and the second distance may be the same, which may provide for redundancy of measurements obtained using the electrical conductivity multiprobe device. In one embodiment, the first distance $D_{302}$ is between 7 mm and 9 mm, including all ranges, subranges, values, and endpoints thereof, and the second distance $D_{304}$ is between 14 mm and 20 mm, including all ranges, subranges, values, and endpoints thereof, and these distances may generally be referred to as electrode pair spacing distances. Of course, other electrode pair spacing distances may be used for the first and second electrical conductivity probes 302, 304.

Turning to FIG. 5, and with continued reference to FIG. 4, there is shown the electrical conductivity multiprobe device 300, which is shown in FIG. 5 as further including a handle 320, connectors 322, a flame deflector 324, and an elongated housing 326 that houses the electrical conductivity probes 302, 304 or at least portions thereof. The handle 320 is shown as a T-shaped handle and may be formed of metal; however, it should be appreciated that various handles, handle configurations, and handle materials may be used for the handle 320. The connectors 322 are high temperature ceramic connectors and one connector may be matching the type of thermocouple chosen.

The flame deflector 324 is used to prevent heat and/or matter (e.g., particulate matter, liquid) from reaching the connector 322 and/or an operator that may hold the electrical conductivity multiprobe device 300 by the handle 320. The flame deflector 324 is depicted as an annular ring that encircles the elongated housing 326. The flame deflector 324 may be made of any suitable material, such as metal. Various different shapes and configurations may be used for the flame deflector 324 as the annular ring structure and configuration shown in FIG. 5 is but one example.

The elongated housing 326 houses (at least portions of) the electrical conductivity probes 302, 304, namely electrical conductivity probe wiring that is used to connect the electrodes 312-318 of the electrical conductivity probes 302, 304 to the processor 306. The elongated housing 326 may also house (at least portions of) the thermocouple(s) 308, such as wiring used to connect the sensor of the thermocouple(s) 308 to the processor 306. As shown in FIG. 5, the electrodes 312-318 and the thermocouple sensing element (or sensor) 328 of the thermocouple(s) 308 each extends past an end 330 of the elongated housing 326 so that, in operation when the end 330 of the electrical conductivity multiprobe device 300 is immersed into the conductive liquid, the electrical conductivity probes 302, 304 and thermocouple(s) 308 may contact the conductive liquid and capture sensor data, such as an electrical resistivity or conductivity (for the electrical conductivity probes 302, 304) and temperature (for the thermocouple(s) 308). The bottom end 330 may also be referred to as a probe end or an electrode end as it is an end that is used for obtaining measurements using the electrodes and, in at least some embodiments, includes portions of the electrodes and/or thermocouple(s) 308 that are exposed to the conductive liquid (L).

The elongated housing 326 is shown as an elongated cylinder extending along a longitudinal axis A from the bottom or probe end 330 to a top end 332 at which the connectors 322 are connected. The elongated housing 326 may be made from any suitable material or combination of materials, such as from one or more ceramics, metals, polymers, or other materials suitable for immersion in the conductive liquid. According to embodiments, the elongated housing 326 may be shaped or structured differently.

Figure 6A:
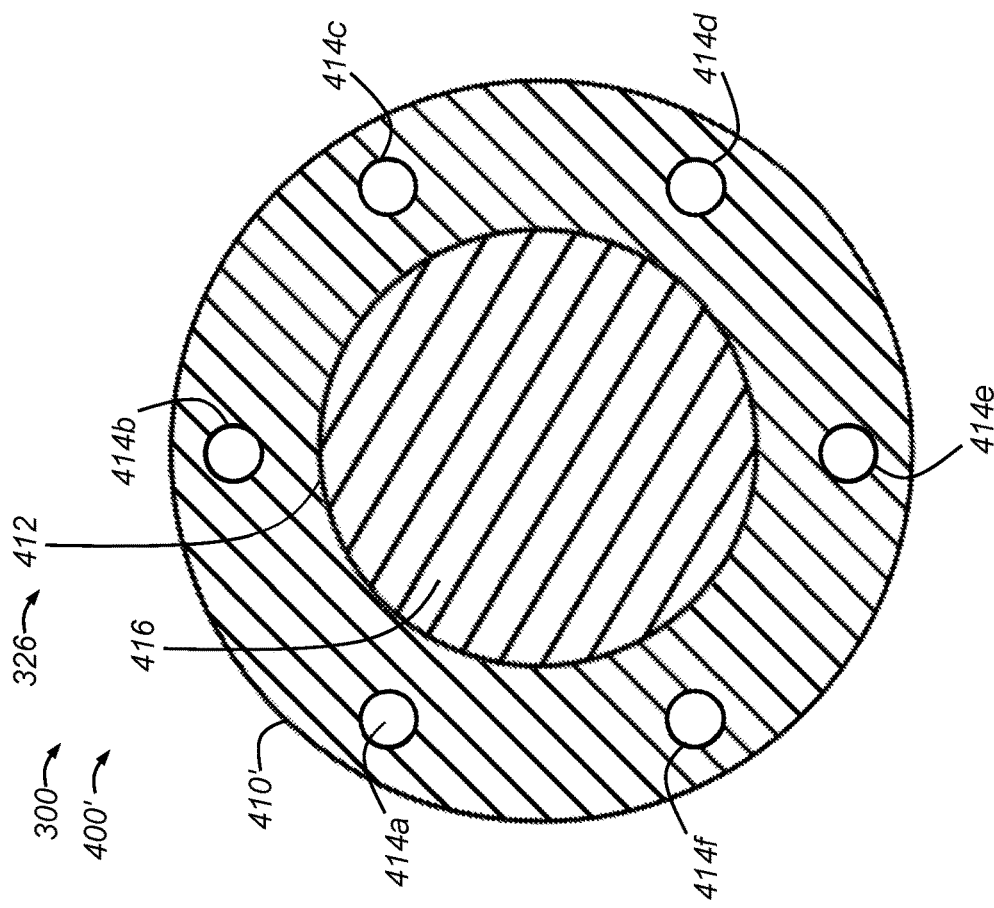
FIG. 6A is a sectional view taken along 6-6 of FIG. 5 showing portions of electrical conductivity probes included in the electrical conductivity multiprobe device of FIG. 4, according to one embodiment employing a first electrical conductivity multiprobe device configuration.

Turning now to FIG. 6A, there is shown a sectional view of the electrical conductivity multiprobe device 300 and, more particularly, a sectional view taken at section 6-6, which is orthogonal to the longitudinal axis A, as shown in FIG. 5. The sectional view of FIG. 6A depicts a first electrical conductivity multiprobe device configuration 400 that is used by the electrical conductivity multiprobe device 300 according to the depicted embodiment. However, it should be appreciated that various other electrical conductivity multiprobe device configurations may be used for the electrical conductivity multiprobe device 300, and such a configuration may be selected according to particulars in which the electrical conductivity multiprobe device 300 is to be used and/or according to the particular or desired numbers of electrical conductivity probes and thermocouples.

According to the electrical conductivity multiprobe device configuration 400, the elongated housing 326 is a unitary or one-piece cylindrical structure comprised of a single body 410 that may be comprised of a high purity polycrystalline alumina ($Al_2O_3$) material; it may be possible to use other alumina ceramics or other materials, according to embodiments and depending on the particular conductive liquid and operating conditions employed. In the second electrical conductivity multiprobe device configuration 400' (FIG. 6B), the single body 410' is cylindrical in shape and includes a central bore 412 that extends through a central axis so the body 410' forms a tube-like structure. The body 410, 410' includes six bores 414a-f that extend the length of the body 410, 410' and that may be configured to receive one or more wires and, in one embodiment, a single wire, such as a single solid-core wire. In some embodiments, the body 410, 410' with wires used to form a part of electrode leads may be formed by shoving or forcing the wires through the bores 414a-f.

Figure 6B:
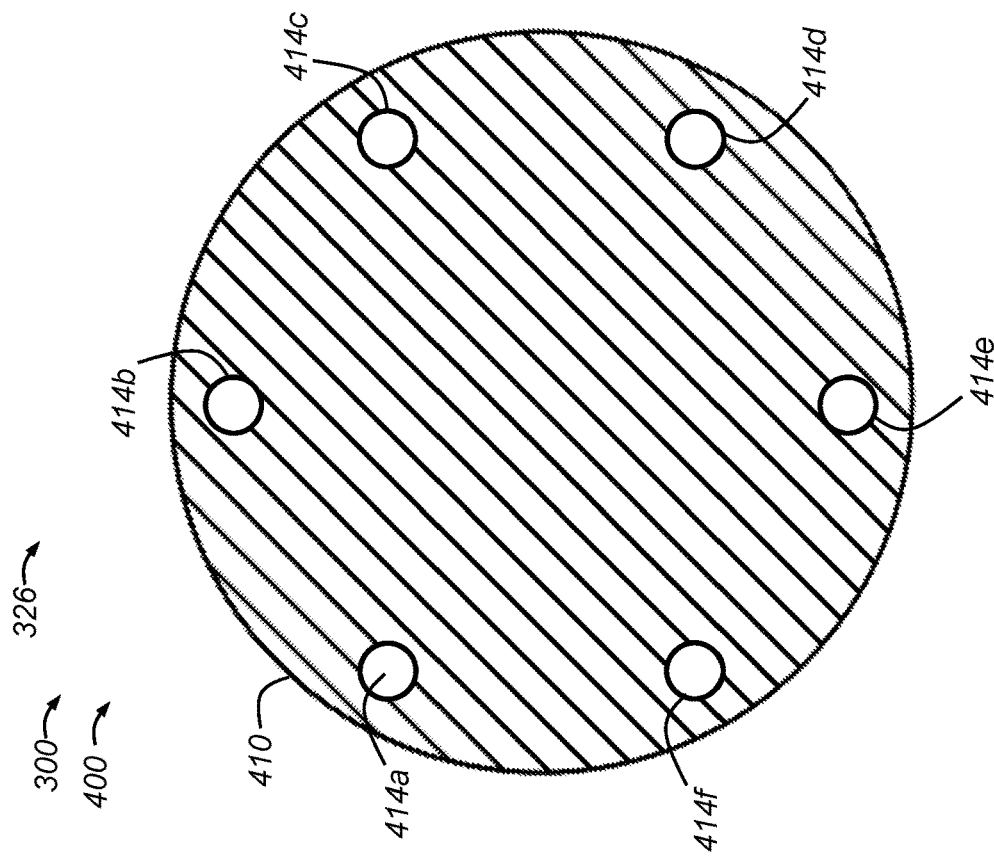
FIG. 6B is a first alternative sectional view taken along 6-6 of FIG. 5 showing portions of electrical conductivity probes included in the electrical conductivity multiprobe device of FIG. 4, according to one embodiment employing a second electrical conductivity multiprobe device configuration.

With reference now specifically to FIG. 6B, in some embodiments, the central bore 412 may be filled wholly or at least partially with material, such as another blank or piece of alumina ceramic, such as high purity polycrystalline alumina ($Al_2O_3$) material, which is referred to as a plug 416. The plug 416 may serves to keep glass out of the center of the tube which would crack the tube on cooling due to differences in thermal expansion coefficients. Of course, according to embodiments and depending on the particular conductive liquid and operating conditions employed, various materials may be employed and different shapes, sizes, and configurations may be used and adapted to the environment and implementation in which the probe device 300 is being used.

With reference to FIGS. 6A and 6B, the bores 414a-f may carry four electrode wires for two probes, such as for the electrodes 312-318 of the electrical conductivity probes 302, 304, and wiring for the thermocouple(s) 308. In one embodiment, a spacing of approximately 19 mm or ¾" is used as the spacing between the electrodes. In one embodiment, the diameter of the body 410, 410' is 1" or about 25 mm; however, according to embodiments and depending on the particular conductive liquid and operating conditions employed, various different shapes, sizes, and configurations may be used for the body 410, 410".

Figure 6D:
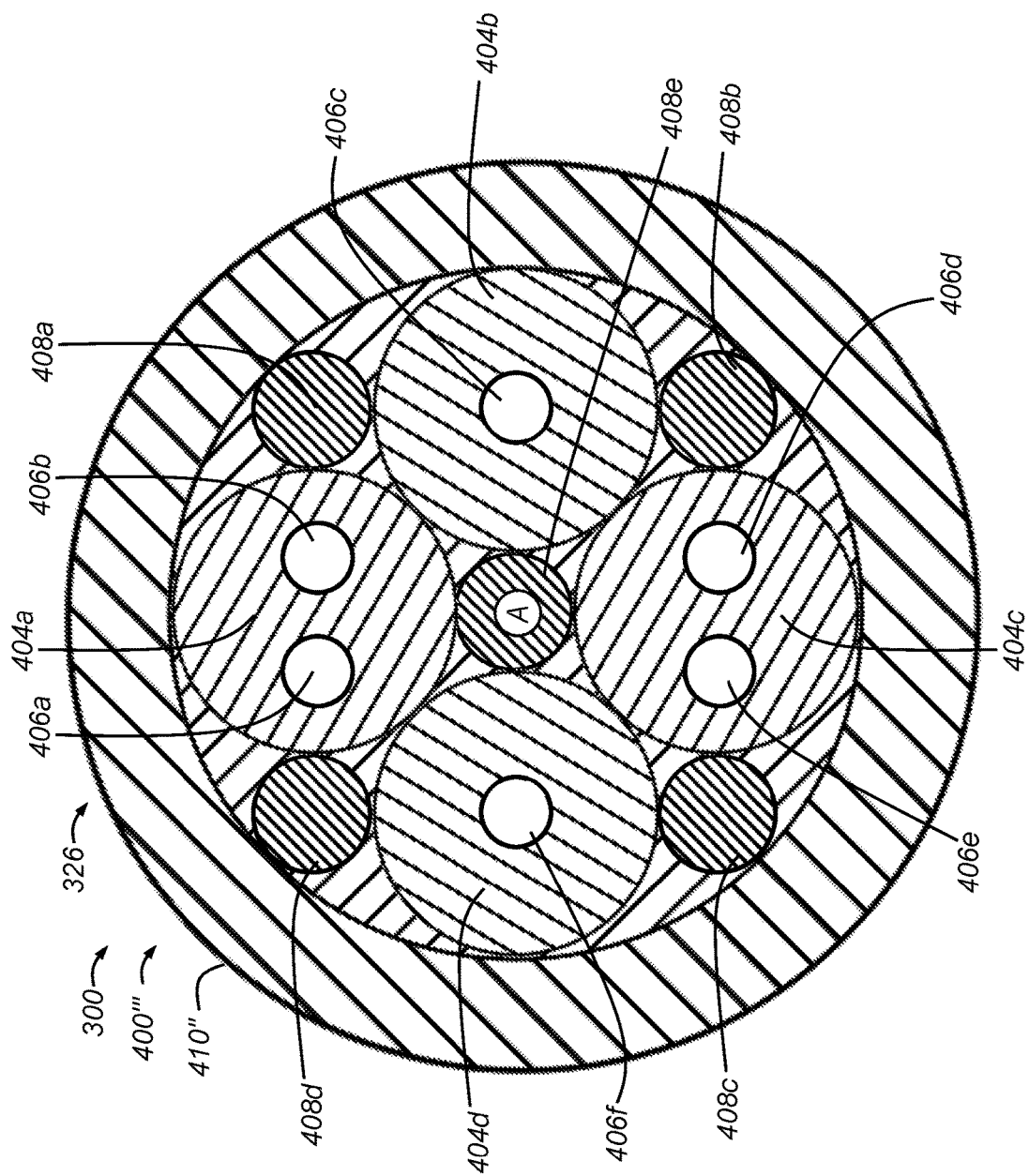
FIG. 6D is a third alternative sectional view taken along 6-6 of FIG. 5 showing portions of electrical conductivity probes included in the electrical conductivity multiprobe device of FIG. 4, according to one embodiment employing a fourth electrical conductivity multiprobe device configuration and a second tube in a tube construction.

Turning now to FIGS. 6C and 6D, there are shown embodiments of a sectional view of the electrical conductivity multiprobe device 300 and, more particularly, a sectional view taken at section 6-6, of the electrical conductivity multiprobe device 300 according to another embodiment in which a third electrical conductivity multiprobe device configuration 400" is employed (FIG. 6C) and yet another embodiment in which a fourth electrical conductivity multiprobe device configuration 400"' is employed (FIG. 6D). In the third electrical conductivity multiprobe device configuration 400" (FIG. 6C), the elongated housing 326 includes a main housing or body 410" that forms an exterior and main body of the elongated housing 326. The main housing 410" is circular in cross section, as shown in FIG. 6C, and encircles and houses a plurality of conduits or tubes 404a-d, each of which contains portions of one or more of the electrical conductivity probes 302, 304 and thermocouple(s) 308. In particular, as depicted in FIG. 6C, the elongated housing 326 includes four tubes 404a, 404b, 404c, 404d with the first tube 404a containing portions of the first electrode 312 and the second electrode 314 of the first electrical conductivity probe 302; the second tube 404b containing portions of the first electrode 316 of the second electrical conductivity probe 304; the third tube 404c containing portions of the thermocouple(s) 308; and the fourth tube 404d containing portions of the second electrode 318 of the second electrical conductivity probe 304. In one embodiment, the main housing or body 410" and tubes 404a-d are each made from a ceramic material, such as from solid alumina rods; however, other materials may be used. According to one embodiment, the main housing or body 410" has an outer diameter of 0.75" and an inner diameter of 0.50" and each of the tubes 404a-d has an outer diameter of ³⁄₁₆" and each bore 406a-f has a diameter of 0.04"; however, of course, the size, shape, material, number, and configuration of these components may differ. In embodiments, each of the electrodes 312-318 and/or the thermocouple(s) 308 may include wiring within one or more bores of the tubes 404a-d and may have an outer diameter of 0.02" (24 AWG) and be comprised of a platinum or platinum, alloy wire; however, of course, the size, shape, material, number, and configuration of the wiring used for the electrodes 312-318 and/or the thermocouple(s) 308 may differ. Each of the main housing or body 410" and tubes 404a-d is shaped as an elongated cylinder in the depicted embodiment; however, it should be appreciated that any suitable shapes or structures may be used, such as an elongated uniform or regular hexagonal prism, for example.

As shown in FIG. 6C, each of tubes 404a and 404c is a dual-bore tube that includes two (or dual) bores and each of tubes 404b and 404d is a single-bore tube that includes a single bore. In particular, dual-bore tube 404a includes a first bore 406a and a second bore 406b, single-bore tube 404b includes a first or single bore 406c, dual-bore tube 404c includes a first bore 406d and a second bore 406e, and single-bore tube 404d includes a first or single bore 406f. Each of the bores 406a-f extends generally parallel to the longitudinal axis A and is coextensive in length with the elongated housing 326.

According to one embodiment, wiring of the first electrode 312 and wiring of the second electrode 314 of the first electrical conductivity probe 302 are contained in the first bore 406a and the second bore 406b of the dual-bore tube 404a, respectively. And, in embodiments, wiring of the thermocouple(s) 308 (e.g., wiring of a first one of the thermocouple(s) 308) is contained in the first bore 406d and the second bore 406e of the dual-bore tube 404c. In embodiments, each of bores 406a-f includes a single wire, each of which may be a solid wire.

Turning now to FIG. 6D, there is shown another embodiment of a sectional view of the electrical conductivity multiprobe device 300 and, more particularly, a sectional view taken at section 6-6, of the electrical conductivity multiprobe device 300 according to another embodiment in which a second electrical conductivity multiprobe device configuration 400" is employed. In this embodiment, a plurality of studs 408a-c (namely, five studs 408a-c in the depicted embodiment of FIG. 6D) is introduced into spaces between the tubes 404a-d. In at least one embodiment, these studs 408a-e may be used to provide structural support and/or integrity to the device 300. In one embodiment, the studs 408a-e are each made from a ceramic material, such as from solid alumina rods; however, other materials may be used. Moreover, the rods may have an outer diameter of 0.08"; however, of course, the size, shape, material, number, and configuration of the studs 408a-e may differ.

With reference to FIG. 7, the method 500 begins at step 510, wherein an initial volume of the conductive liquid (L) is determined. In some embodiments, the initial volume of the conductive liquid (L) is determined by measuring a liquid level of the conductive liquid (L) using the liquid level sensor and a known capacity or volume of the crucible or vessel in which the conductive liquid is held. For example, a look up table or volumetric equation may be developed or known for the crucible that is usable to obtain a conductive liquid (L) volume based on the liquid level of the conductive liquid (L) when in the crucible. In other embodiments, the volume of the conductive liquid (L) is after step 520 and after introducing the conductive liquid (L) into the crucible. The method 500 continues to step 520.

In embodiments, the method 500 includes heating the conductive liquid (L) is heated at a known temperature and this step is analogous to the step 210 of the method 200 above. In one embodiment, the crucible, which includes glass material, is heated inside of a constant temperature furnace operating at a temperature of 1350° C. This step may be carried out prior to step 510, after step 510 and prior to step 520, or at any other suitable time.

In step 520, gas is introduced into the conductive liquid and, in at least some embodiments, an amount of gas being introduced into the conductive liquid is known and/or recorded. In embodiments, gas may be introduced into a zone of the conductive liquid that is below a solid porous layer or other bubble conditioning layer, such as through a metered gas inlet. The initial volume of glass and/or conductive liquid and the volume of the gas at the calibration temperature allow a gas volume fraction to be determined, which may be carried out in step 540. The method 500 continues to step 530.

In step 530, the first electrode and the second electrode of the electrical conductivity probe are inserted into a measurement zone of the conductive liquid (L) after the molten glass has been heated for a period of time and is beginning to fine the gas bubbles. In some embodiments, the electrical conductivity probe, and in particular, each of the first electrode and the second electrode of the electrical conductivity probe, is preheated so as to mitigate detrimental effects caused by thermal shock when the electrical conductivity probe is introduced into the heated conductive liquid (L). The method 500 then proceeds to step 540.

In step 540, a gas volume fraction of the conductive liquid is determined. In at least some embodiments, a volume of the conductive liquid (L) is determined and used with the initial volume (step 510) to determine the gas volume fraction. In at least one embodiment, the volume may be determined by determining a liquid level of the conductive liquid (L) and then using that with known information about the crucible. The liquid level may be measured by the liquid level sensor. The method 500 proceeds to step 550.

In step 550, the probe measures voltages at a first node and a second node relative to a common node, such as that described above with respect to step 230, to determine resistance information, which may be represented by a resistance as discussed herein. The method 500 proceeds to step 560, wherein the measured voltages and/or information derived or based thereon (e.g., a resistance as described herein) may be determined and then stored along with the determined gas volume fraction. These stored values may thus be used as a reference later for determining a gas volume fraction that corresponds to a particular resistance determined by the probe. The resistances and the corresponding gas volume fractions associated with each resistance value can be stored in memory accessible by the probe. The method 500 then may end.

In some embodiments, the method 500 further includes obtaining temperature information using one or more thermocouples, such as one or more thermocouples of the electrical conductivity probe device. The method 500 may further include storing in memory the obtained temperature information with the resistance information and/or the gas volume fraction. The obtained temperature information may be used in conjunction with the resistance information to determine a gas volume fraction of a conductive liquid in operation.

It should be appreciated that the method 500 may be used with any of the above-described electrical conductivity probe devices, including any of the above-described electrical conductivity multiprobe devices. It should be appreciated that this method 500 may be used for a calibration process, such as the calibration process 202 of the method 200, and then the stored information may then be used for determining a gas volume fraction when in an operating mode.

According to other embodiments, any one or more of the preceding methods and/or systems may be employed in combination with one another, provided such combination is technically feasible and not inconsistent with the discussion herein.

According to some embodiments, any one or more of the preceding methods and/or systems, including any of their technically-feasible combinations, may further include and/or be characterized by any one of, or any technically-feasible combination of two or more of, the following features:
  an end of the first electrode or an end of the second electrode is larger than a gas bubble in the conductive liquid;
  the first electrode and the second electrode are a part of an electrical conductivity probe device and each extend along a longitudinal axis, and wherein the electrical conductivity probe device is positioned in an orientation in which the longitudinal axis is not vertically aligned relative to gravity;
  the conductive liquid comprises molten glass;
  a step of immersing the first electrode and the second electrode in molten glass at a constant temperature;
  a step of measuring one or more resistances by immersing the first electrode and the second electrode in a different conductive liquid with a known gas volume fraction and determining the resistance between the first electrode and the second electrode when immersed in the different conductive liquid;
  the first electrode and the second electrode are moved in the liquid and a plurality of measurements of the electrical resistance of the conductive liquid are taken;

the first electrode includes a first immersion paddle and the second electrode includes a second immersion paddle;

the first electrode is connected to the voltage source via the resistor, and wherein the resistance information includes a first voltage measurement that is taken across the resistor and a second voltage measurement that is taken across the first electrode and the second electrode;

the processor measures one or more resistances while the first electrode and the second electrode are immersed in a different conductive liquid with a known gas volume fraction and determines the resistance between the first electrode and the second electrode when immersed in the different conductive liquid;

the first electrode and the second electrode are immersed in the conductive liquid at a constant temperature;

the electrical conductivity probe device is an electrical conductivity multiprobe device having a first electrical conductivity probe and a second electrical conductivity probe, wherein the first electrical conductivity probe includes the first electrode and the second electrode and the second electrical conductivity probe includes a pair of electrodes referred to as a third electrode and a fourth electrode;

the first electrical conductivity probe and the second electrical conductivity probe are provided within a common housing;

the common housing is formed of an elongated tube;

the first electrode, the second electrode, the third electrode, and the fourth electrode project axially past an end of the common housing;

a thermocouple that is provided in the common housing;

the common housing includes a plurality of tubes housing the first electrical conductivity probe and the second electrical conductivity probe;

the plurality of tubes includes a first tube having a pair of bores including a first bore and a second bore, and wherein the first electrode is disposed within the first bore and the second electrode is disposed within the second bore;

the plurality of tubes includes a first tube and a second tube, and wherein the third electrode is disposed within a bore of the first tube and the fourth electrode is disposed within a bore of the second tube;

a handle usable by an operator for positioning, moving, and/or orienting an electrode end, which has a measurement portion of the first electrode and the second electrode, of the electrical conductivity probe device;

a flame deflector oriented between the handle and the electrode end of the electrical conductivity probe device;

heating the conductive liquid prior to the measuring steps; and/or the resistance information is or includes a resistance that is determined based on the first voltage and the second voltage It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation. In addition, the term "and/or" is to be construed as an inclusive OR. Therefore, for example, the phrase "A, B, and/or C" is to be interpreted as covering all of the following: "A"; "B"; "C"; "A and B"; "A and C"; "B and C"; and "A, B, and C."

The invention claimed is:

1. A method of determining a gas volume fraction in a conductive liquid, comprising:
    (a) immersing a first electrode in the conductive liquid, wherein the first electrode is electrically connected to a resistor and a voltage source, and wherein the conductive liquid comprises molten glass;
    (b) immersing a second electrode electrically connected to the voltage source in the conductive liquid;
    (c) determining resistance information indicative of an electrical resistance of the conductive liquid between the first electrode and the second electrode; and
    (d) determining a gas volume fraction in the conductive liquid based on the measurement.

2. The method of claim 1, wherein an end of the first electrode or an end of the second electrode is larger than a gas bubble in the conductive liquid.

3. The method of claim 1, wherein the first electrode and the second electrode are a part of an electrical conductivity probe device and each extend along a longitudinal axis, and wherein the electrical conductivity probe device is positioned in an orientation in which the longitudinal axis is not vertically aligned relative to gravity.

4. The method of claim 1, further comprising the step of immersing the first electrode and the second electrode in molten glass at a constant temperature.

5. The method of claim 1, further comprising the step of measuring one or more resistances by immersing the first electrode and the second electrode in a different conductive liquid with a known gas volume fraction and determining the resistance between the first electrode and the second electrode when immersed in the different conductive liquid.

6. The method of claim 1, wherein the first electrode and the second electrode are moved in the liquid and a plurality of measurements of the electrical resistance of the conductive liquid are taken.

7. The method of claim 1, wherein the first electrode is connected to the voltage source via the resistor, and wherein the resistance information includes a first voltage measurement that is taken across the resistor and a second voltage measurement that is taken across the first electrode and the second electrode.

8. A method of determining a gas volume fraction in a conductive liquid, comprising:
    (a) immersing a first electrode in the conductive liquid, wherein the first electrode is electrically connected to a resistor and a voltage source;
    (b) immersing a second electrode electrically connected to the voltage source in the conductive liquid;

(c) periodically measuring a first voltage at the first node relative to a common node and a second voltage at a second node relative to the common node; (d) determining a plurality of resistances using the periodically measured first voltages and the periodically measured second voltages;

(e) associating a gas volume fraction with each resistance;

(f) storing the resistances and the associated gas volume fractions in a memory device;

(g) immersing the first electrode and the second electrode in a different conductive liquid;

(h) measuring a first voltage at the first node relative to a common node and a second voltage at a second node relative to the common node while the first electrode and the second electrode are immersed in the different conductive liquid;

(i) determining a resistance based on the first voltage and second voltage measured while the first electrode and second electrode are immersed in the different conductive liquid;

(j) comparing the resistance determined during step (i) with the stored resistances and associated gas volume fractions;

(k) identifying a stored resistance that matches the resistance determined during step (i); and (l) determining a gas volume fraction associated with the identified stored resistance.

9. The method of claim 8, wherein an end of the first electrode or an end of the second electrode is larger than a gas bubble in the conductive liquid.

10. The method of claim 8, wherein the first electrode and the second electrode are not vertically aligned.

11. The method of claim 8, wherein the conductive liquid comprises molten glass.

12. The method of claim 8, further comprising the step of immersing the first electrode and the second electrode in molten glass at a constant temperature.

13. The method of claim 8, wherein the first electrode includes a first immersion paddle and the second electrode includes a second immersion paddle.

14. An electrical conductivity probe device for measuring a gas volume fraction in a conductive liquid, comprising:
- a first electrode that is electrically connected to a resistor and a voltage source;
- a second electrode electrically connected to the voltage source; and
- a processor configured to obtain a first voltage measurement across a first node on the first electrode and a common node on the first electrode and a second voltage measurement across a second node on the second electrode and the common node, wherein the processor: determines an electrical resistance of the conductive liquid based on the first voltage measurement and the second voltage measurement when the first electrode and the second electrode are immersed in the conductive liquid; and determines a gas volume fraction in the conductive liquid based on the measurement, and wherein the conductive liquid comprises molten glass.

15. The electrical conductivity probe device of claim 14, wherein an end of the first electrode or an end of the second electrode is larger than a gas bubble in the conductive liquid.

16. The electrical conductivity probe device of claim 14, wherein the first electrode and the second electrode are not vertically aligned.

17. The electrical conductivity probe device of claim 14, wherein the processor measures one or more resistances while the first electrode and the second electrode are immersed in a different conductive liquid with a known gas volume fraction and determines the resistance between the first electrode and the second electrode when immersed in the different conductive liquid.

18. The electrical conductivity probe device of claim 14, wherein the first electrode and the second electrode are immersed in the conductive liquid at a constant temperature.

19. The electrical conductivity probe device of claim 14, wherein the electrical conductivity probe device is an electrical conductivity multiprobe device having a first electrical conductivity probe and a second electrical conductivity probe, wherein the first electrical conductivity probe includes the first electrode and the second electrode and the second electrical conductivity probe includes a pair of electrodes referred to as a third electrode and a fourth electrode.

20. The electrical conductivity probe device of claim 19, wherein the first electrical conductivity probe and the second electrical conductivity probe are provided within a common housing.

21. The electrical conductivity probe device of claim 20, wherein the common housing is formed of an elongated tube.

22. The electrical conductivity probe device of claim 20, wherein the first electrode, the second electrode, the third electrode, and the fourth electrode project axially past an end of the common housing.

23. The electrical conductivity probe device of claim 20, further comprising a thermocouple that is provided in the common housing.

24. The electrical conductivity probe device of claim 20, wherein the common housing includes a plurality of tubes housing the first electrical conductivity probe and the second electrical conductivity probe.

25. The electrical conductivity probe device of claim 24, wherein the plurality of tubes includes a first tube having a pair of bores including a first bore and a second bore, and wherein the first electrode is disposed within the first bore and the second electrode is disposed within the second bore.

26. The electrical conductivity probe device of claim 24, wherein the plurality of tubes includes a first tube and a second tube, and wherein the third electrode is disposed within a bore of the first tube and the fourth electrode is disposed within a bore of the second tube.

27. The electrical conductivity probe device of claim 14, further comprising a handle usable by an operator for positioning, moving, and/or orienting an electrode end, which has a measurement portion of the first electrode and the second electrode, of the electrical conductivity probe device.

28. The electrical conductivity probe device of claim 14, further comprising a flame deflector oriented between the handle and the electrode end of the electrical conductivity probe device.

* * * * *

UNITED STATES PATENT AND TRADEMARK OFFICE
CERTIFICATE OF CORRECTION

PATENT NO. : 12,320,767 B2
APPLICATION NO. : 18/106000
DATED : June 3, 2025
INVENTOR(S) : Lawrence Gochberg et al.

Page 1 of 1

It is certified that error appears in the above-identified patent and that said Letters Patent is hereby corrected as shown below:

In the Claims

Claim 1, Column 16, Line 32: replace "...measurement." with "...resistance information."

Claim 3, Column 16, Line 38: replace "...extend..." with "...extends..."

Claim 8, Column 17, Line 1: replace "...the first node..." with "...a first node..."

Claim 8, Column 17, Line 7: replace "...each resistance;" with "...each resistance of the plurality of resistances;"

Claim 8, Column 17, Line 8: replace "...storing the resistances..." with "...storing the plurality of resistances..."

Claim 14, Column 17, Lines 57-58: replace "...the measurement..." with "...the electrical resistance..."

Claim 28, Column 18, Line 58: replace "...claim 14,..." with "...claim 27,..."

Signed and Sealed this
First Day of July, 2025

Coke Morgan Stewart
*Acting Director of the United States Patent and Trademark Office*